US00PP12211P2

(12) United States Plant Patent
Akerboom

(10) Patent No.: US PP12,211 P2
(45) Date of Patent: Nov. 20, 2001

(54) ASTER PLANT NAMED 'M.C. SNOWY'

(75) Inventor: Petrus J. Akerboom, Ter Aar (NL)

(73) Assignee: De Nachtvlinder B.V., Ter Aar (NL)

( * ) Notice: Subject to any disclaimer, the term of this patent is extended or adjusted under 35 U.S.C. 154(b) by 0 days.

(21) Appl. No.: 09/263,155

(22) Filed: Mar. 5, 1999

(51) Int. Cl.[7] ..... A01H 5/00
(52) U.S. Cl. ..... Plt./355
(58) Field of Search ..... Plt./355

(56) References Cited

U.S. PATENT DOCUMENTS

P.P. 10,783 * 2/1999 Akerboom ..... Plt./355

OTHER PUBLICATIONS

UPOV–ROM GTITM Computer Database 2000/02, GTI JOUVE Retrieval Software, citations for 'M.C. Snowy', May 2000.*

* cited by examiner

*Primary Examiner*—Bruce R. Campell
*Assistant Examiner*—Wendy C Baker
(74) *Attorney, Agent, or Firm*—C. A. Whealy

(57) ABSTRACT

A distinct cultivar of potted Aster plant named 'M.C. Snowy', characterized by its medium plant height at flowering; freely and uniform flowering; decorative inflorescence form with white ray florets; and good post-production longevity.

2 Drawing Sheets

BACKGROUND OF THE INVENTION

The present invention relates to a new and distinct cultivar of Aster plant, botanically known and *Aster novi-belgii* and referred to by the cultivar name M.C. Snowy.

The new Aster is a product of a planned breeding program conducted by the Inventor in Ter Aar, The Netherlands. The objective of the breeding program was to create new cut flower Asters having desirable floret colors, uniform flowering and numerous inflorescences.

The new Aster originated from a cross made in 1995 by the Inventor of a *Aster novi-belgii* unidentified proprietary Aster selection as the female, or seed, parent with the Inventor's proprietary selection code No. MC 206 as the male, or pollen, parent.

The cultivar M.C. Snowy was discovered and selected by the Inventor as a flowering plant within the progeny of the stated cross in a controlled environment in Ter Aar, The Netherlands.

Asexual reproduction of the new Aster by terminal cuttings taken at Ter Aar, The Netherlands, has shown that the unique features of this new Aster are stable and reproduced true to type in successive generations of asexual reproduction.

SUMMARY OF THE INVENTION

The following traits have been repeatedly observed and are determined to be the unqiue characteristics of 'M.C. Snowy'. These characteristics in combination distinguish 'M.C. Snowy' as a new and distinct cultivar:

1. Freely and uniform flowering.
2. Decorative inflorescence form with white ray florets.
3. Good post-production longevity.

Plants of the new Aster can be compared to plants of the Aster cultivar Peter's White, disclosed in U.S. Plant Pat. No. 10,783. In side-by-side comparisons conducted in Ter Aar, The Netherlands, plants of the new Aster differed from plants of the cultivar Peter's White in the following characteristics:

1. Plants of the new Aster are slightly taller than plants of the cultivar Peter's White.
2. Leaves of the new Aster are shorter and more narrow than leaves of the cultivar Peter's White.
3. Plants of the new Aster have smaller but more numerous inflorescences than plants of the cultivar Peter's White.
4. Inflorescences of the new Aster develop disc florets whereas inflorescences of plants of Peter's White do not develop disc florets.

The cultivar M.C. Snowy has not been observed under all possible environmental conditions. The phenotype may vary somewhat with variations in environment such as temperature, daylength and light intensity, without, however, any variance in genotype.

BRIEF DESCRIPTIONS OF THE PHOTOGRAPHS

The accompanying colored photographs illustrate the overall appearance of the new Aster, showing the colors as true as it is reasonably possible to obtain in colored reproductions of this type. Colors in the photographs may differ slightly from the color values cited in the detailed botanical description which more accurately describe the actual colors of the new Aster.

The photograph on the first sheet comprises a side perspective view of typical flowering stem of the new Aster.

The photograph on the second sheet comprises a close-up view of typical inflorescences of the new Aster.

DETAILED BOTANICAL DESCRIPTION

In the following description, color references are made to The Royal Horticultural Society Colour Chart except where general terms of ordinary dictionary significance are used. The following observations and measurements describe plants grown during the summer in Ter Aar, The Netherlands, in a glass-covered greenhouse with average day temperatures of 17 to 35° C. and night temperatures of 14 to 20° C. Plants received long day/short night treatments 18 hours light for seven weeks and then were forced into flower with short day/long night treatments 12 hours light.

Botanical classification: *Aster novi-belgii* cultivar M.C. Snowy.

Commercial classification: Cut flower Aster.

Parentage:

*Male or pollen parent.*—Proprietary *Aster novi-belgii* seedling selection, code No. MC 206.

*Female or Seed parent.*—Unidentified proprietary *Aster novi-belgii* selection.

Propagation:

*Type.*—Terminal tip cuttings.

*Time to initiate roots.*—About 8 to 10 days at a temperature of 18 to 23° C.

*Time to develop roots.*—Summer: About 16 to 20 days at a temperature of 23° C. Winter: About 20 to 25 days at a temperature of 18° C.

*Root description.*—Fine, fibrous and well-branched.

Plant description:

*Appearance.*—Herbaceous cut flower. Stems upright; medium plant height at flowering. Freely and uniformly flowering; white decorative inflorescences.

*Crop time.*—About 13.5 to 14 weeks from planting to harvest of cut flowering stems.

*Branching habit.*—Freely branching, typically more than 30 lateral branches per plant.

*Growth rate.*—Slow.

*Plant height.*—About 80 to 90 cm.

*Plant width.*—About 45 cm.

*Lateral branch length.*—At the top of the flowering stem, about 80 to 90 cm above soil level: About 3 to 5 mm. At the middle of the flowering stem, about 40 to 45 cm above soil level: About 24 to 37 cm. At the bottom of the flowering stem, about 15 to 25 cm above soil level: About 4 to 14 mm.

*Lateral branch diameter.*—At the top of the flowering stem, about 80 to 90 cm above soil level: About 0.4 to 0.6 mm. At the middle of the flowering stem, about 40 to 45 cm above soil level: About 1.8 to 2.3 mm. At the bottom of the flowering stem, about 15 to 25 cm above soil level: About 0.7 to 1.3 mm.

*Internode length.*—At the top of the flowering stem, about 80 to 90 cm above soil level: About 4 to 6 mm. At the middle of the flowering stem, about 40 to 45 cm above soil level: About 2.4 to 3.6 cm. At the bottom of the flowering stem, about 15 to 25 cm above soil level: About 3 to 4.7 cm.

*Stem color.*—Light green, 144A to 146A no anthocyanin at internodes.

*Stem texture.*—Moderately pubescent.

*Foliage description.*—Arrangement: Alternate. Quantity: At the top of the flowering stem, about 80 to 90 cm above soil level: Few. At the middle of the flowering stem, about 40 to 45 cm above soil level: About 24 to 37. At the bottom of the flowering stem, about 15 to 25 cm above soil level: About 2 to 8. Shape: Linear; apex acute; base attenuate, sessile; margin entire. Size: At the top of the flowering stem, about 80 to 90 cm above soil level: About 1 to 1.4 cm in length and about 1.2 to 1.4 mm in width. At the middle of the flowering stem, about 40 to 45 cm above soil level: About 10 to 12.3 cm in length and about 2.2 to 5.2 cm in width. At the bottom of the flowering stem, about 15 to 25 cm above soil level: About 10.4 to 14.2 cm in length and about 4.1 to 6.2 cm in width. Texture: Glabrous, leathery. Color: Young leaves, upper surface: 147A. Young leaves, lower surface: 146C. Fully expanded leaves, upper surface: 147A. Fully expanded leaves, lower surface: 146B. Venation, upper and lower surfaces: 145C.

Flowering description:

*Appearance.*—Decorative inflorescence form. Flattened inflorescences, held on wiry peduncles arising from leaf axils; inflorescences face upright. Disc and ray florets arranged acropetally on a capitulum.

*Flowering response.*—Under natural conditions, plant flower in the late summer/autumn. At other times of the year, inflorescence initiation and development can be induced under short day/long night conditions. Response time is about 6 to 6.5 weeks.

*Post-production longevity.*—Good, inflorescences last about 3.5 to 4.5 weeks on the plant; about 2 to 3 weeks as a cut flower without postproduction treatments. Inflorescences persistent.

*Quantity of inflorescences.*—Inflorescences form at every leaf axil. Freely flowering, usually more than 200 inflorescences per flowering stem.

*Fragrance.*—None.

*Inflorescence size.*—Diameter: About 2.9 cm. Disc diameter: About 4 mm. Depth (height): About 3.5 to 6.2 mm.

*Inflorescence bud.*—Shape: Cylindrical. Length: About 4.5 to 5.5 mm. Diameter: About 5.1 to 6.1 mm. Color: 146B.

*Ray florets.*—Quantity of ray florets per inflorescence: About 143. Shape: Narrowly obovate; apex rounded; base attenuate; margin entire. Length: About 1.3 cm. Width: About 9 to 15 mm. Texture: Satiny, smooth and glabrous. Color: When opening, upper surface: 155B. When opening, lower surface: 155B. Mature, upper surface: 155B to 155D. Mature, lower surface: 155B to 155D.

*Disc florets.*—Quantity: About 14 per inforescence. Shape: Elliptic. Length: About 3.5 to 4.1. Width: About 0.8 mm. Color: Immature: Light yellow 154A. Mature: Yellow 9A.

*Peduncle.*—Strength: Strong. Length: Apical peduncle: About 1 to 5 mm. Fourth peduncle: About 2 to 4 mm. Seventh peduncle: About 2 to 5 mm. Color: 146A to 147A.

*Reproductive organs.*—Androecium: Present on disc florets only. Quantity of stamens: One per floret. Filament length: Less than one millimeter. Filament color: White. Anther size: About 3.6 to 4.2 mm. Pollen: Scarce; yellow in color 12A. Gynoecium: Present on both ray and disc florets. Pistil length: About 3 to 3.8 mm. Stigma color: 10C to 10D. Style length: About 2.2 mm.

*Seed development.*—Not observed.

Disease resistance: Plants of the new Aster have not been observed to be resistant to pathogens common to Asters, however plants of the new Aster appear to be less sensitive to Powdery Mildew than other known cultivars of Aster.

It is claimed:

1. A new and distinct cultivar of Aster plant named 'M.C. Snowy', as illustrated and described.

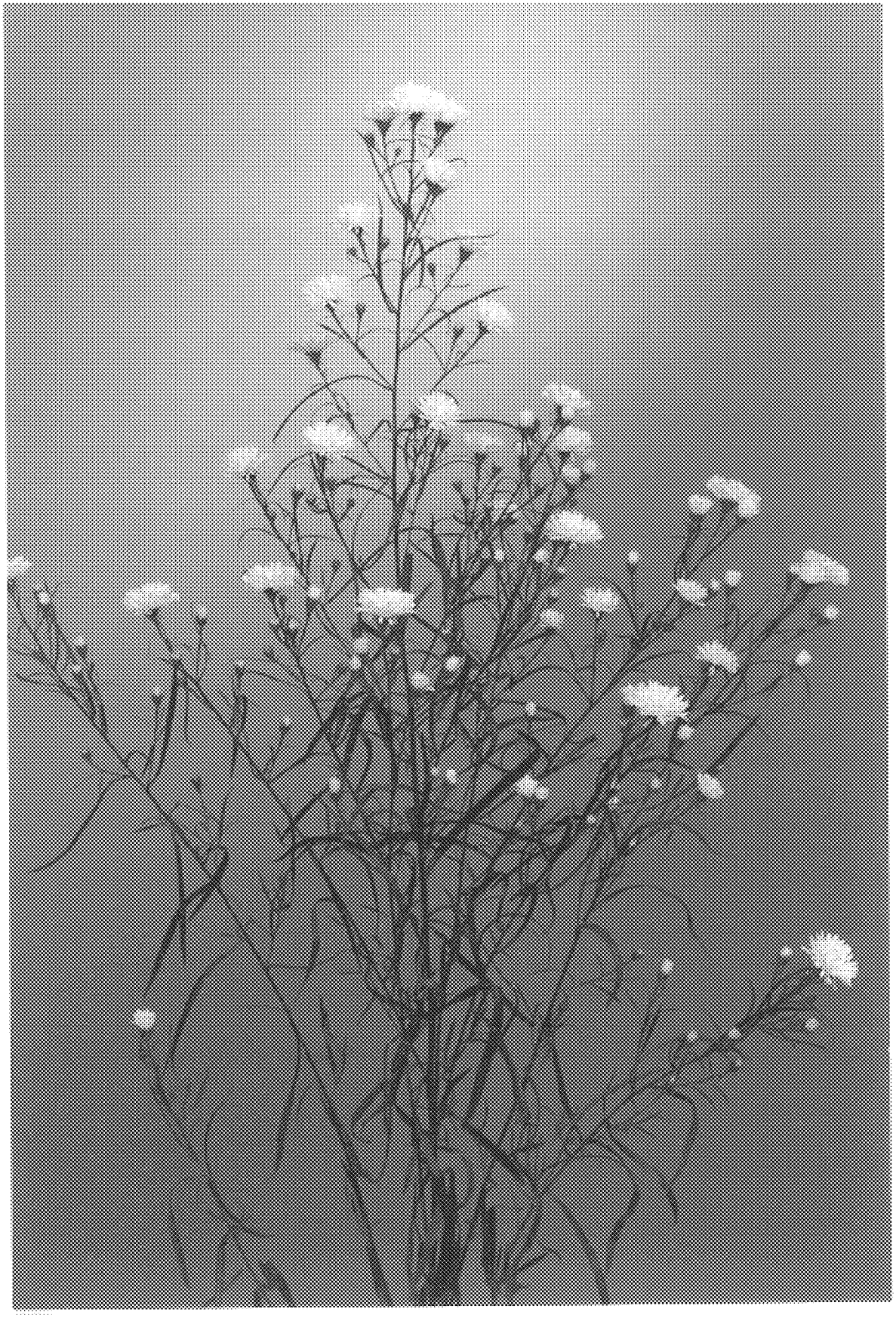

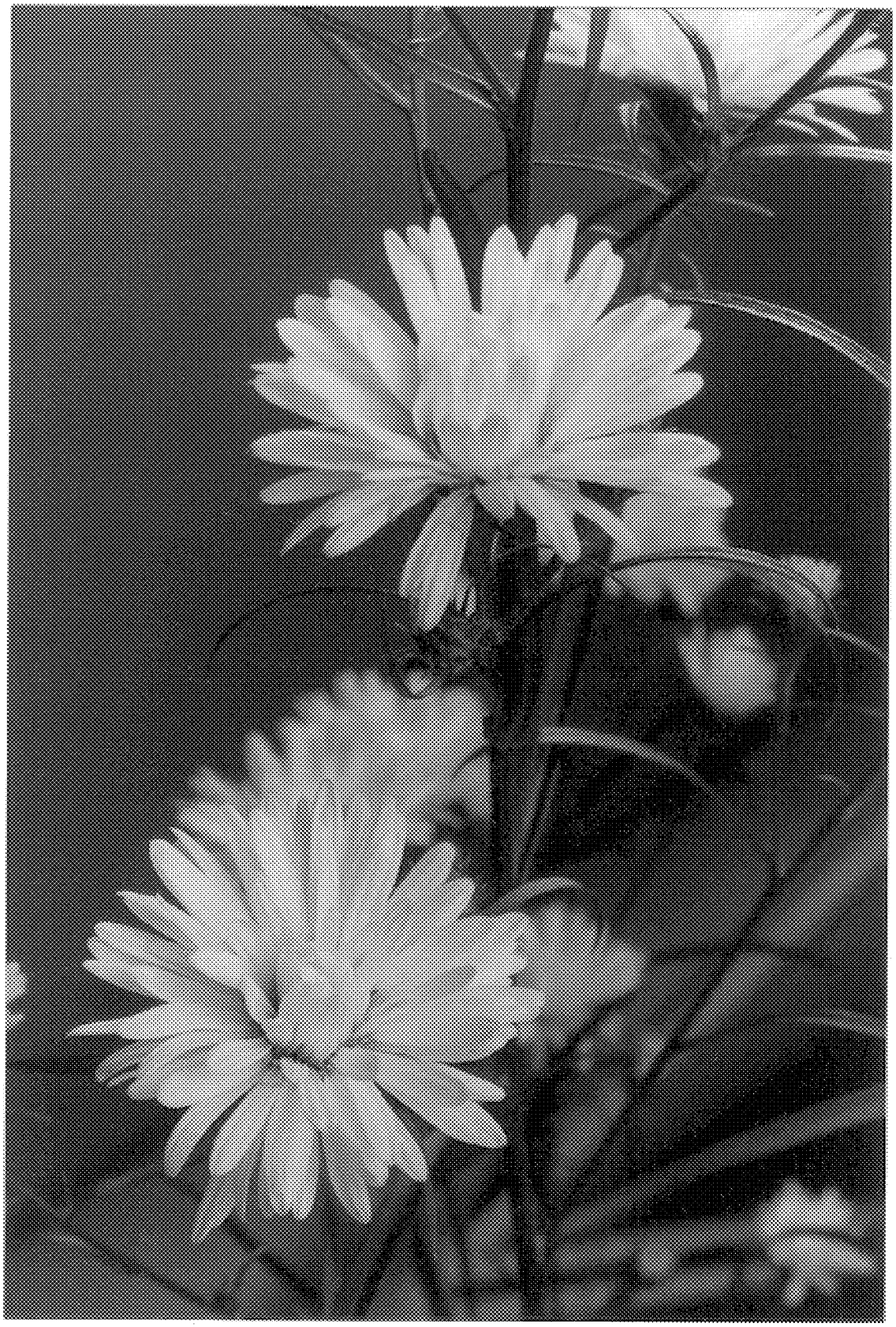

* * * * *